United States Patent [19]

Mondeil et al.

[11] Patent Number: 4,720,196
[45] Date of Patent: Jan. 19, 1988

[54] METHOD AND APPARATUS FOR MEASURING THE HEATING POWER OF COMBUSTIBLE GASES

[75] Inventors: Lucien Mondeil, Morlaas; Francois Robert, Trespoey Prolongée, both of France

[73] Assignee: Societe Nationale Elf Aquitaine (Production), France

[21] Appl. No.: 875,600

[22] Filed: Jun. 18, 1986

[30] Foreign Application Priority Data

Jun. 18, 1985 [FR] France ............................... 85 09238

[51] Int. Cl.⁴ ............................................. G01N 25/40
[52] U.S. Cl. ............................................. 374/37; 374/1
[58] Field of Search ..................... 374/35, 36, 37, 24, 374/27, 8, 38; 165/104.2

[56] References Cited

U.S. PATENT DOCUMENTS

| | | | |
|---|---|---|---|
| 1,268,196 | 6/1918 | Wilsey et al. | 374/35 |
| 2,743,609 | 5/1956 | Schuller | 374/36 |
| 2,825,226 | 3/1958 | Daley, Jr. et al. | 374/36 |
| 3,301,059 | 1/1967 | Haas | 374/35 |
| 4,386,858 | 1/1983 | Kude et al. | 374/37 |

*Primary Examiner*—Daniel M. Yasich
*Attorney, Agent, or Firm*—Ostrolenk, Faber, Gerb & Soffen

[57] ABSTRACT

A method and apparatus for measuring the heating power of a combustible gas. The ratio of the temperature of gases entering and exiting a calorimeter is maintained substantially equal to 1, and the entering air is maintained at its water saturation limit. The calorimeter comprises two concentric cells having a central chimney closed at the top and housing a burner. A coiled tube discharges gases from the chimney. Two temperature probes transmit signals to a microprocessor which actuates a heat exchanger provided in an external wall of the outermost concentric cell.

12 Claims, 2 Drawing Figures

METHOD AND APPARATUS FOR MEASURING THE HEATING POWER OF COMBUSTIBLE GASES

BACKGROUND OF THE INVENTION

1. Field of the Invention

The present invention relates to a method and apparatus for the continuous measurement of the caloric value of a combustible gas.

More specifically, the caloric value or heating power of a gas is measured by a calorimeter having a central chimney housing a burner, a means for supplying the combustible gas at a given pressure and flow rate, and two annular concentric cells. The external wall of the external cell is provided a heat exchanger for regulating its temperature. The concentric cells are separated by an annular dividing wall parallel to the cell of walls and are connected to a differential pressure sensor.

2. Description of the Related Art

A calorimeter of this general type is disclosed in French patent application No. 81 18722, published Apr. 5, 1983 (corresponding to U.S. Pat. No. 4,500,214) in the joint name of Onera and the present inventor. In this calorimeter, the internal and external cells have small thicknesses with respect to their length. Thus, the temperature gradient formed in the cells is substantially normal to the walls. These cells are concentric and annular. Convection currents are practically nonexistent and the heat flow passes through the calorimeter in a substantially radial direction without being disturbed by upward and downward movements of convection.

Measurement of the thermal flow is made by a different gas thermometer. Two cells are filled with the same gas and separated by a dividing wall having a certain thermal resistance. Heat passes radially through the wall inducing a temperature rise in the cells. The difference of the voluminal integral of the temperatures in each cell is proportional to the heat flow released by the combustion of a combistive gas. Thus, the difference of the pressure existing in each cell is proportional to the flow according to the following formula:

$$\Delta P = K_1 \Delta \theta = K_2 \Psi$$

where:

$\Delta \theta$ is the mean temperature difference in the cells; and, $\omega$ is the heat flow due to the combustive gas.

However, when measuring the heat content of a gas, care must be taken that the calorimeter measures only the latent condensation heat of the water formed by combustion of the gas. The prior art obtains incorrect readings because of the latent condensation of water contained in the initial combustive air. Also, the non-condensation of a part of the water formed by combustion and the non-saturation of the combustion air produces inaccurate readings.

In the present invention, we assume:

$$\Delta P = K_3 \cdot q_g \cdot PCS_g$$

where:

$q_g$ is the flow rate of the combustible gas; and,
$PCS_g$ is the heat content of the gas.

SUMMARY OF THE INVENTION

An object of the present invention is therefore to provide a calorimeter which obtains the latent heat of condensation of the water formed by combustion of gas.

Another object of the present invention is to provide a calorimeter which obtains only the latent heat of condensation of the water formed by combustion of a gas.

A further object of the present invention is to provide a calorimeter which generally obtains truer readings than the prior art devices.

The present invention achieves the foregoing objectives by providing a calorimeter which maintains the temperatures and flow rates of a reference gas and a gas whose heat content is to be determined, the same. The temperatures of the flow of the gases are maintained the same by the addition of work to the system. The heat content of the gas being measured is determined from the amount of work required to maintain the gases at the same temperature.

Other features and advantages of the present invention are described below with reference to the accompanying drawings.

DESCRIPTION OF THE DRAWINGS:

The features of the invention will be clear from the following description of the invention given by way of example and illustrated by the accompanying drawings in which.

DETAILED DESCRIPTION OF THE INVENTION

Figure 1:
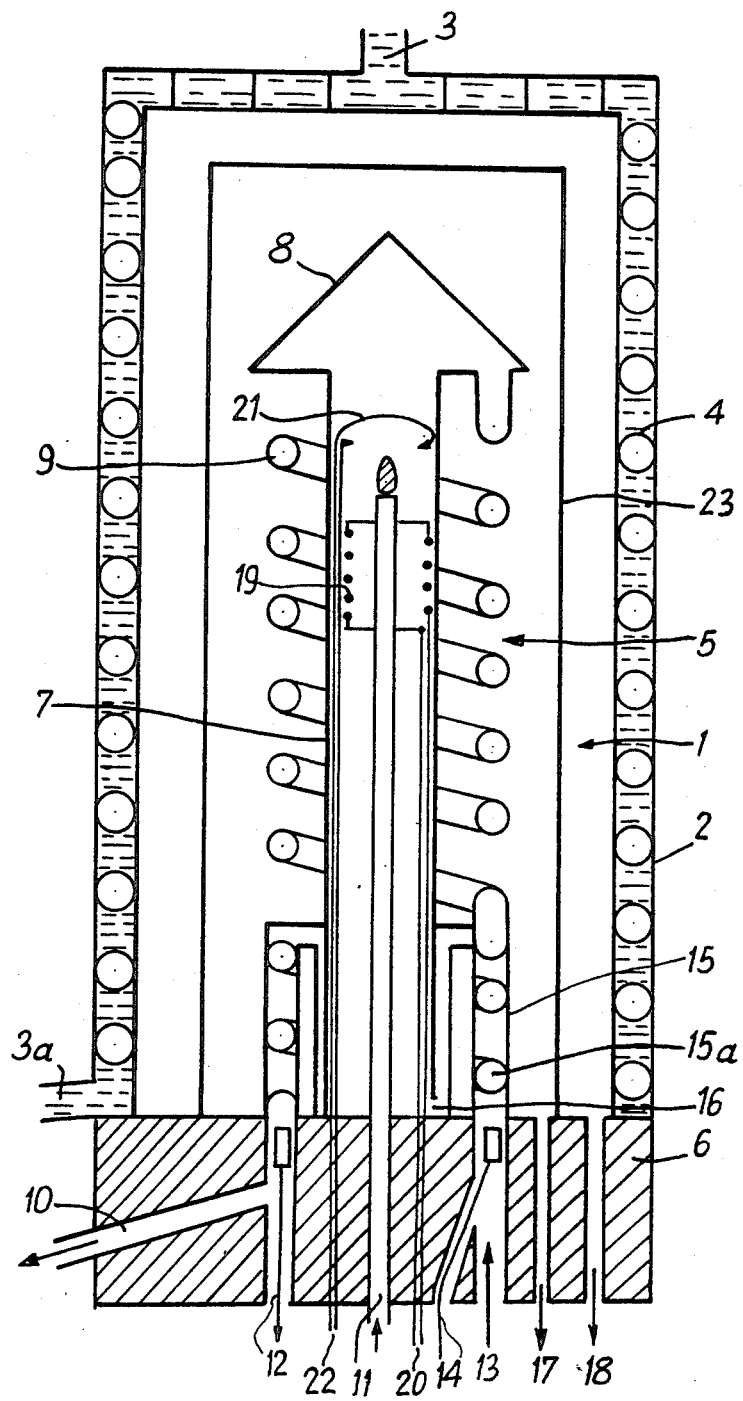
FIG. 1 illustrates the calorimeter of the present invention in an axial section; and, FIG. 2 shows a general diagram of the invention.

The method of the present invention maintains the ratio of the output temperature of burnt gases to that of the temperature of input gases substantially close to 1. Also, the degree of saturation of the combustive air feeding the burner is kept at its water saturation limit. Thus, only the latent condensation heat of the water formed by the combustion and the total heat flow emitted by the combustion of the gas is measured.

Keeping the output temperature of burnt gas very close to the input temperature of the supplied gas, and keeping the degree of saturation of the air at the limit of saturation prevents any error in heat content measurement which might be due to:

(1) any inflow of humidity in the combustive air causing an excess of condensation;

(2) any saturation of the combustive air causing a lack of condensation; and (3) any poor input/output gas temperature ratio causing over-condensation, or under-condensation.

By keeping the gas temperature ratio close to 1, the influence of the water contained in the air is cancelled out, so that it is the same saturation which occurs in the output gases. Thus, only the water formed by the combustion is condensed and measured in the calorimeter.

Preferably, the ratio of the burnt gas output temperature to that of the input gas is kept at a value slightly greater than 1, for example, between 1.02 and 1.05. Thus, despite the contraction of gas volume following combustion, the water vapor entering the system in the saturated combustive air is kept in the vapor state in the outgoing burnt gases without undergoing condensation. Thus, only the exact amount of water formed by combustion is condensed.

If the gas having a reduced gas volume following combustion is kept at the same temperature as the input gas temperature, for example 40° C., addditional condensation of water would occur. Thus, an incorrect measurement would result.

However, by holding of the gas output temperature at a value slightly greater than that of the input gas, for example, at 41.5° C., the heat content of this additional condensed water is avoided in the measurement.

The present invention also avoids any heat exchange error which is variable with time. When the heat content of the gases vary, for example for a reference gas to a sample gas, the heat losses also vary in time and an incorrect measurement is obtained. To overcome such effects, the operation is carried out in accordance with the invention under constant thermal flow using the method of the present invention which overcomes any possible non-linearities of the pressure sensor used for measuring the value of the flows.

Also, according to another feature of the invention, measuring the heat content of the sample gas $PCS_g$ is alternated with calibration of the calorimeter. This is accomplished by measuring the known heat content of a reference gas $PCS_r$, followed by measuring the heat content of the sample gas $PCS_g$.

This is accomplished by bringing the value of the heat flow for each measurement to a given constant value by supplying heat energy $W_g$ to the sample gas and heat energy $W_r$ to the reference gas. This heat energy is supplied by an additional heating resistance element, with the gas flow rate of the sample gas $q_g$ and the gas flow rate of the reference gas $q_r$, constant and equal. Thus, the heat content of the sample gas is determined by rearranging the following equation:

$$qr \cdot PCS_r + W_r = q_g \cdot PCS_g + W_g$$

to:

$$PCS_g = PCS_r + W_r - W_g/q_g$$

This expression is a function of measured values of complementary externally supplied heat energies $W_r$ and $W_g$, thus avoiding errors due to non-linearities of the differential pressure sensor. Also, the equality of the heat flows is provided by adjusting the power added to the system so as to maintain the signal of the differential pressure sensor constant.

In a preferred embodiment, during an initial calibration phase, the value of the total flow transmitted is brought to a constant value $\Psi_c$. This is achieved by adding to the flow emitted by combustion of the reference gas $\Psi_{cr}$, heat enery $W_r$ and maintaining the ratio of the burnt gas output temperatures to that of the input gases at a value close to 1. Maintaining the ratio close to 1 is achieved by adding heat via the heat exchanger in the external wall of the external cell. In the measurement phase, the value of the total flow transmitted is brought to the same value $\Psi_c$ by a heat energy supply $W_g$ which is added to the flow emitted by the combustion of the gas to be measured $\Psi_{cg}$.

Preferably, the flow rate equality provided during calibration and during measurement is controlled by the differential phase measurements $\Delta P$ of the sensor connector to the two cells of the calorimeter. The gas flow rate during the calibration and measurement phases is maintained constant by using a precision displacement pump. The pump is fed with gas at a regulated pressure and is emersed in a bath of regulated temperature. Furthermore, the pump speed is controlled by an electronic power supply of very high stability.

The calorimeter of the present invention comprises a central chimney housing a burner. The chimney is supplied with combustible gas and combustive air at a given pressure and flow rate. Also, two annular concentric cells are provided. The external wall of the external cell is provided with a heat exchanger. The concentric cells are separated by an annular dividing wall parallel to the cell walls and are connected to a differential pressure sensor. The central chimney is closed at the top and gas in the chimney escapes through a coil tube which surrounds the external wall of the chimney, and whose opposite end emerges outside the calorimeter for discharging the burnt gases. A temperature probe is disposed in contact with the burnt output gases and another probe is in contact with the input gases. The probes are connected to a processing unit for processing their signals. The processing unit is provided with a circuit for actuating the heat exchanger in the external wall of the external cell.

Preferably, the lower part of the coil tube is housed in an indirect heat exchanger for causing the counter current flow of the gases feeding the burner.

Such an arrangement maintains the gas temperature ratio close to 1.

A displacement pump is connected to a sample gas intake duct (having a pressure regulator) and to the burner of the calorimeter. An air humidifier is connected to an air intake duct (having a flow regulator) and to the central tube of the calorimeter. The displacement pump, a majority of the air and sample gas intake ducts, and the humidifier are maintained in a thermostat controlled bath.

An electric resistance heating element is housed in the central chimney of the calorimeter. Also, the two cells of the calorimeter are connected by piping to a differential pressure sensor associated with a processing unit for actuating a circuit controlling the power supply to the resistance heating element.

A tube feeding the burner with combustion gas opens into the upper part of the central chimney.

Referring now to FIG. 1, the calorimeter comprises two annular concentric cells 1 and 5. The annular concentric cell 1 contains the reference gas and is bordered by the outer double wall 2 and the annular concentric wall 23. The annular concentric cell 5 contains the sample gas and is bordered by annular concentric wall 23 and the tubular chimney 7. The external cell 1 has an outer double wall 2 containing baffles 4. Water flows in the outer double wall 2 of external reference cell 1 through duct 3 such that the outer double wall 2 acts as a heat exchanger with the reference gas contained in reference cell 1. Water exits the double wall through duct 3a. The two cells 1 and 5 are located on base 6.

A tubular chimney 7 is located along the longitudinal central axis of the sample cell 5. One end of chimney 7 rests on base 6 and the other end is closed by a cap 8. The inside of cap 8 communicates with coiled pipe 9, coiled about the outer wall of chimney 7 and serving for discharging the combustion products to the outlet through duct 10 formed in base 6. Base 6 houses a heat probe 12 for measuring the outgoing gas temperature TS. Inside the chimney, in the upper part, combustible gas is introduced via duct 11 formed in the base. Combustive air is introduced through duct 13 formed in base 6. A temperature probe 14 for measuring the inlet air temperature is located in duct 13. A heat exchanger 15 exchanges heat from the burnt gases flowing through coiled tube 15A with air entering chimney 7 through opening 16.

Channels 17 and 18 open respectively into cells 5 and 1, and are connected through base 6 to a differential pressure sensor for measuring the valve of $\Delta P$.

In the upper part of chimney 7, a concentric resistance element 19 surrounds combustible gas intake tube 11. Element 19 is connected to a power supply source through conducting wires 20 and maintains a constant heat flow.

An ignition spark gap 21 is located at the upper end of chimney 7 and is connected through concurrent conducting wires 22 to a power supply (not shown).

Figure 2:
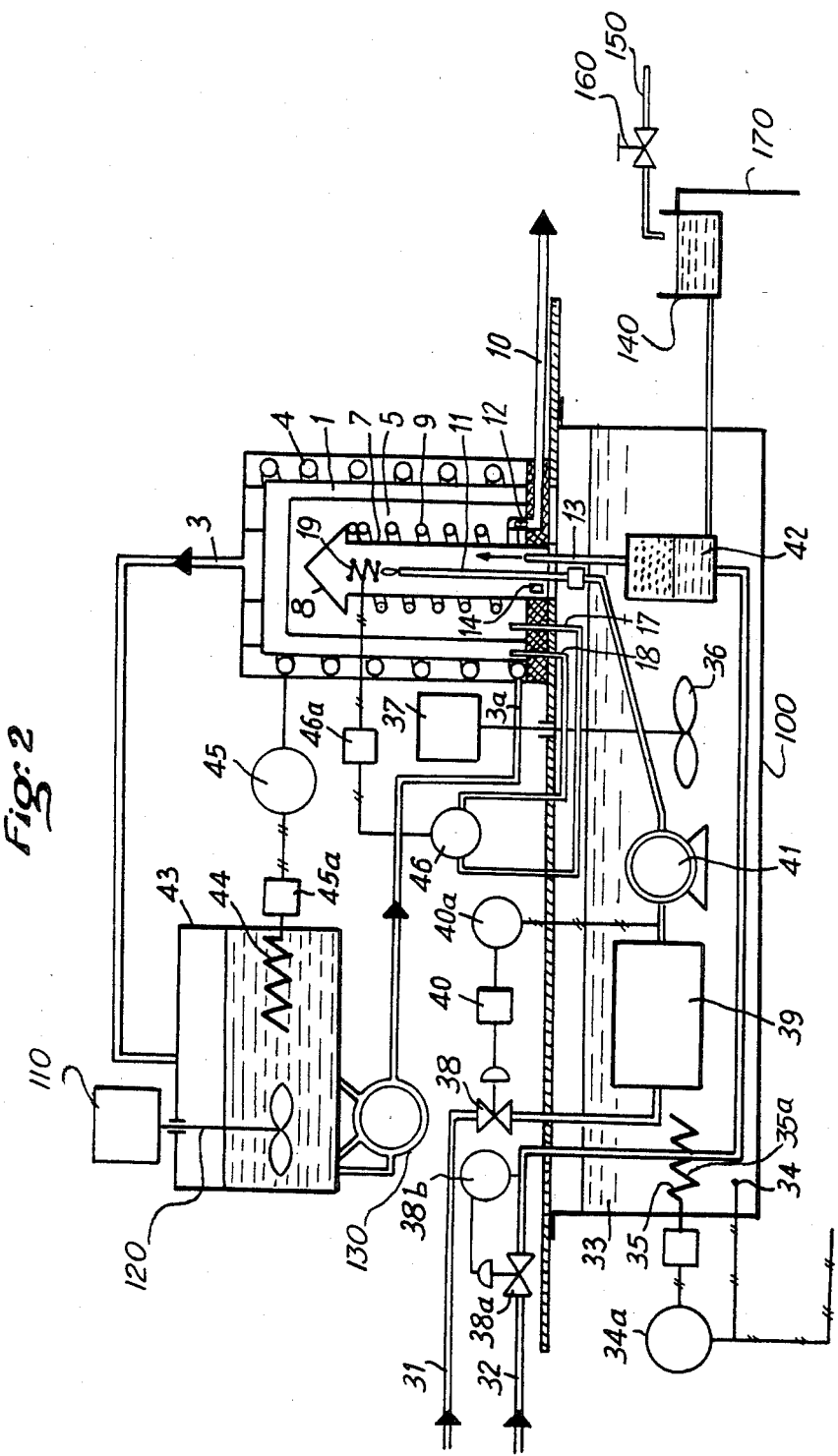

Referring now to FIG. 2, the above described calorimeter is illustrated in a complete system. Gas and air is supplied through two ducts 31 and 32 which pass through a gas temperature stabilization bath 100. The bath 33 may be oil, and the bath temperature is controlled by means of a temperature probe 34, a regulator 34a and a heating resistance unit 35 which has a resistive heating element 35a. The bath is stirred by a stirring system 36, driven by a motor 37.

Combustion gas inlet 31 provides combustion gas to chimney 7. Valve 38 is located in combustion gas inlet 31 and is controlled by a pressure regulator 40 receiving signals from pressure sensor 40a. Combustion gas is provided through inlet 31 and collects in reservoir 39 followed by pumping to chimney 7 via pump 41. Pump 41 is a rotary pump whose rotational speed is controlled by a stable current supply, for example an electric generator. The air circuit comprises duct 32 containing valve 38A controlled by a flow rate regulator 38b and a humidifier 42 providing for total air saturation. Humidifier 42 is supplied from water reservoir 140, which has overflow run off 170. Reservoir 140 is in turn supplied by water inlet 150 being controlled by valve 160. Water is supplied to external heat exchanger 2 of the calorimeter through duct 3, and then flows to stir tank 43 whose temperature is regulated by means of a temperature probe 45. Regulator 45a measures the temperature of the external exchanger 2 and controls a heating resistance element 44 placed in the tank 43. The tank is stirred by stirrer 120, controlled by motor 110. Pump 130 controls the water flow.

The differential pressure $\Delta P$ is measured by means of a sensor 46. Regulator 46a receives signals from sensor 46 and controls heating resistance element 19 disposed inside the chimney 7.

A microprocessor (not shown) receives the following information: the pressure of the displacement pump 41, the temperature of the gas temperature stabilization bath, the differential pressure $\Delta P$ of cells 1 and 5, the temperature of the external exchanger and the input temperature TE of the burner and the output temperature TS of the burnt gases. The microprocessor then actuates the following: gas flow control valve 38 and air flow control valve 38a, the heating circuits 35 of the bath 33, the water tank heating element 44 and the heating resistance element 19 placed above the burner, using regulation algorithms to maintain the input and output gas temperature.

In operation, during the calibration phase, reference gas is introduced into the apparatus, which by burning gives a reference heat content gr PCSr. Additional heating power Wr is provided via resistance element 19, which is supplied with power so that the total power produced is equal to a predetermined value.

When the apparatus is stabilized, the outgoing gas temperature $T_s$ is brought substantially close to, or slightly greater than the incoming gas temperature TE, such that the ratio of these values is close to 1. This is achieved by modifying the temperature of the external exchanger 2 so as to reduce the ratio TS/TE to the desired value.

For natural gas of ordinary quality and entering at a temperature of 40° C., the outgoing gas temperature is kept at 41.5° C. (ratio TS/TE about 1.027) by means of the external exchanger circuit 2. The differential pressure $\Delta P$, is proportional to the heat flow and can be calculated from the following formula:

$$\Delta P = (q_r PCS_r + W_r) K_3$$

For determining the unknown heat content of the gas (the measurement phase), the gas input is started and the work $W_g$ delivered to the resistance element 19 is adjusted so as to maintain the differential pressure $\Delta P$ equal to the differential pressure observed during calibration. In other words, the equality of the heat flows emitted during the calibration phase and during the measurement phase is achieved by adjusting the power $W_g$ delivered to resistance element 19 so as to keep the signal from the differential pressure sensor 46 at the same value. Once the apparatus is stabilized, this power is measured.

The heat content of the gas to be measured is then calculated by the following formula:

$$PCS_g = PCS_r + W_r - W_g/q_g$$

Although the present invention has been described in connection with the preferred embodiments, many other variations and modifications will now become apparent to those skilled in the art without departing from the scope of the invention. It is preferred, therefore, that the present invention be limited not by the specific disclosure herein, but only by the appended claims.

What is claimed is:

1. A method for continuously measuring the calorific value of a combustible gas utilizing a calorimeter having an annular internal cell containing a reference gas and an annular external cell containing said combustible gas, both of said cells surrounding a central chimney, comprising the steps of:

supplying, to a burner located in said housing, a combustible gas and combustion air, and burning said combustible gas in said burner;

monitoring the pressure differential in said annular internal and external cells by a pressure sensor means, and maintaining said pressure differential substantially constant;

maintaining the ratio of the temperature of the burnt gas exiting said burner to the temperature of said combustion gas being supplied to said burner at a value substantially close to 1 by regulating the amount of heat added to said calorimeter; and, maintaining said combustion air being supplied to said burner at its water saturation limit by passing said combustion air through a humidifier.

2. A method as claimed in claim 1, comprising the step of maintaining said temperature of said exiting burnt gas at a value slightly greater than that of said combustion air being supplied to said burner.

3. A method as claimed in claim 2, further comprising the steps of:
  calibrating said calorimeter by measuring the heating power of said reference gas prior to measuring the heating power of said combustible gas.

4. A method as claimed in claim 3, wherein the heating power of said reference gas and said combustible gas are determined by bringing the value of heat flowing between said inner and external annular cells for said calibrating said measuring to a constant reference value by the addition of heat $W_r$ and $W_g$, so that, with said reference and said combustible gas flow rates $q_r$ and $q_g$ maintained constant, by equalizing the heat flow emitted during said calibration and said measurement in accordance with the equation:

$$q_r \cdot PCS_r + W_r = q_g \cdot PCS_g + W_r$$

where:
  $PCS_r$ is the reference gas calorific value; and
  $PCS_g$ is said combustible gas calorific value,
the value of the calorific value of said combustible gas:

$$PCS_g = PCS_r + W_r - W_g/q_g$$

is expressed as a function of measured values of additional internal heat supplies W and W, thus eliminating errors due to nonlinearities of said differential pressure sensor.

5. A method as claimed in claims 3 and 4, wherein during said calibration of said calorimeter, the heat flow emitted by combustion of the reference gas is brought to a reference value by addition of complementary heat energy, while the ratio of the temperatures of the exiting burnt gas and of the entering gas is maintained at a constant value via heat exchange means with which said external cell is provided and, in the measurement phase, the heat flow emitted is brought to the same reference value by supplying complementary heat energy.

6. The method as claimed in claim 5, wherein the equality of the heat flow during said calibration and during said measurement of the sample gas is controlled by differential pressure measurements ΔP by means of a sensor connected to said inner and said outer annular concentric cells of said calorimeter, so as to maintain said differential pressure measurements ΔP at a constant reference value during said measurements.

7. An apparatus for continuously measuring the calorific value of a combustible gas, which comprises:
  a calorimeter having a central chimney with a closed top forming a housing for a burner and means for supplying the burner with combustible gas and combustive air at a given pressure and flow rate;
  said calorimeter having an inner annular concentric cell and an external annular concentric cell;
  a heat exchange means located in an external wall of said external annular concentric cell for supplying heat to said calorimeter;
  said concentric cells being separated by an annular dividing wall parallel to said inner annular concentric cell and concentric cell;
  a differential pressure sensor connected to both said inner annular concentric cell and said external annular concentric cell;
  a coiled tube for discharging burnt gases from said closed top of said chimney, said coiled tube surrounding a external wall of said chimney;
  a first temperature probe in contact with said burnt gases and a second temperature probe in contact with said supply of said combustive air, said first and second temperature probes in communication with a computing unit which activates a circuit for heating said heat exchanger located in said external wall of said external annular concentric cell.

8. An apparatus as claimed in claim 7, further comprising:
  a displacement pump located between an intake duct for said combustion gas having a constant pressure regulator, and said burner of said calorimeter;
  a humidifier located between an intake duct for said combustive air and said central chimney of said calorimeter;
  said displacement pump, said humidifier and a portion of said combustion gas intake duct and said combustive air intake duct being located in a thermostatically controlled bath.

9. An apparatus as claimed in claims 18 or 19, further comprising an electric heating resistance element located in an upper region of said chimney of said calorimeter, and said inner and external annular concentric cells being connected by pipes to said differential pressure sensor which is in communication with means to activate a circuit controlling a power supply connected to said electric heating resistance element.

10. An apparatus as claimed in claims 7, 8 or 9, further comprising a tube for feeding said burner with said combustible gas, said tube opening into said upper region of said chimney.

11. An apparatus as claimed in claims 7, 8, 9 or 10, wherein a lower portion of said coiled tube passes through a second heat exchanger which contains said combustible gas within said tubes and said combustive air outside said tubes.

12. An apparatus as claimed in claims 7, 8, 9, 10 or 11, wherein said displacement pump is controlled by a stable electric supply means.

* * * * *